United States Patent
Ramalingam et al.

(10) Patent No.: US 10,828,328 B1
(45) Date of Patent: Nov. 10, 2020

(54) METHOD OF PREPARING BIOGENIC SILVER NANOPARTICLES

(71) Applicant: KING SAUD UNIVERSITY, Riyadh (SA)

(72) Inventors: R. Jothi Ramalingam, Chennai (IN); Hamad Al Lohedan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/734,152

(22) Filed: Jan. 3, 2020

(51) Int. Cl.
*A61K 33/38* (2006.01)
*A61K 36/21* (2006.01)
*B82Y 40/00* (2011.01)
*B82Y 5/00* (2011.01)

(52) U.S. Cl.
CPC .............. *A61K 33/38* (2013.01); *A61K 36/21* (2013.01); *B82Y 5/00* (2013.01); *B82Y 40/00* (2013.01); *Y10S 977/773* (2013.01); *Y10S 977/81* (2013.01); *Y10S 977/90* (2013.01); *Y10S 977/915* (2013.01)

(58) Field of Classification Search
CPC .......... A61K 33/38; A61K 36/21; B82Y 5/00; B82Y 40/00; Y10S 977/773; Y10S 977/81; Y10S 977/90; Y10S 977/915
See application file for complete search history.

(56) References Cited

FOREIGN PATENT DOCUMENTS

| CN | 104116767 A | 10/2014 |
|----|-------------|---------|
| KR | 1905801 B1 * | 10/2018 |
| RU | 2007146607 A | 6/2009 |

OTHER PUBLICATIONS

Niraimathi KL, et al "Biosynthesis of silver nanoparticles using Alternanthera sessilis (Linn.) extract and their antimicrobial, antioxidant activities" Colloids and Surfaces B: Biointerfaces, Feb. 1, 2013,102,pp. 288-291; doi: 10.1016/j.colsurfb.2012.08.041 (Year: 2018).*

Trung TN, et al "Direct and self-selective synthesis of Ag nanowires on patterned graphene" RSC Advances, 2017, 7, 17325-17331; DOI: 10.1039/c6ra28389f. (Year: 2017).*

Baishya et al., "Biogenesis of Silver Nanoparticles Using Alternanthera Ficoidia Leaf Extract and Its Antibacterial Potential", Int. J. Pharm. Bio. Sci. (2013), vol. 4, No. 3, pp. 104-110.

Firdhouse et al., "Biosynthesis of silver nanoparticles using to extract of Alternanthera sessilis—antiproliferation effect against prostate cancer cells", Cancer Nano. (2013), vol. 4, pp. 137-143.

Pamila et al., "Antimicrobial Activity of Alternanthera bettzickiana (Regel) G. Nicholson and Its Phytochemical Contents", Int. J. Pharm.Sci. Res. (2017), vol. 8, No. 6, pp. 2594-2599.

Petrus et al., "Foliar Biophenolic Antioxidant Metabolites of Alternanthera bettzickiana", Oriental Journal of Chemistry (2014), vol. 30, No. 3, 5 pages.

Nagalingam et al., "Biosynthesis, characterization, and evaluation of bioactivities of leaf extract-mediated biocompatible gold nanoparticles from Alternanthera bettzickiana", Biotechnology Reports (2018), vol. 19, pp. 1-12.

* cited by examiner

*Primary Examiner* — Aaron J Kosar (74) *Attorney, Agent, or Firm* — Nath, Goldberg & Meyer; Richard C. Litman

(57) ABSTRACT

The method of preparing biogenic silver nanoparticles includes preparing an aqueous plant extract by boiling cut leaves of *Alternanthera bettzickiana* (Regel) G. Nicholson in distilled water, retaining the aqueous extract. The aqueous plant extracts were mixed with aqueous solutions of silver ions derived from different silver salt precursors (e.g., silver nitrate, silver sulfate, etc.). The resulting biogenic silver nanoparticles exhibit antimicrobial activity against various strains of gram-positive and gram-negative organisms, including some strains of drug-resistant microorganisms. The biogenic silver nanoparticles also exhibit anticancer activity against certain human cancer cell lines. Surprisingly, biogenic silver nanoparticles prepared from nitrate precursor exhibited greater anticancer activity than nanoparticles from sulfate precursor, while biogenic silver nanoparticles prepared from sulfate precursor exhibited greater antibacterial activity than nanoparticles from nitrate precursor.

11 Claims, 10 Drawing Sheets

METHOD OF PREPARING BIOGENIC SILVER NANOPARTICLES

BACKGROUND

1. Field

The disclosure of the present patent application relates to nanotechnology, and particularly to a method of preparing biogenic silver nanoparticles that exhibit antibacterial and anticancer properties.

2. Description of the Related Art

The antimicrobial properties of silver and silver compounds have been known since ancient times. Silver was used to prevent the growth of bacteria in drinking water by the ancient Egyptians and Persians, and Hippocrates recommended its use on open wounds to prevent infection. Silver remained an important antimicrobial agent until the discovery of antibiotics. The emergence of strains of microorganisms resistant to drugs and the development of nanotechnology has brought renewed interest in silver, and particularly in silver nanoparticles. Silver appears to be effective, even against drug-resistant strains of microbes, and the small size of silver nanoparticles (1 nm to 100 nm) provides a greater surface area per unit volume that makes silver nanoparticles a very efficient antimicrobial agent.

Although silver nanoparticles may be prepared by physical and chemical means, there is great interest in synthesizing silver nanoparticles by reducing silver ions using plant extracts to make biogenic silver nanoparticles. The reduced silver particles may agglomerate with compounds extracted from the plants to make a nanocomposite with the biologically derived compounds coating or modifying the surface of the silver nanoparticles, rendering them more stable physically and chemically. When the compounds extracted from the plant also exhibit antibacterial or therapeutic properties, the biogenic silver nanoparticles may exhibit a synergistic effect, being more effective than either the silver nanoparticles or plant extract used separately, and may also exhibit properties suggesting their use as therapeutic agents for other conditions, e.g., as anti-cancer agents. Even if compounds in the plant extract do not form nanocomposites with the silver nanoparticles, their use in reducing silver ions may result in the formation of nanoparticles of a particular size distribution or particular shapes or configurations that may increase their activity against particular pathogens or disease processes or states. Consequently, there is great interest in developing biogenic silver nanoparticles from plant extracts.

Thus, a method of preparing biogenic silver nanoparticles solving the aforementioned problems is desired.

SUMMARY

The method of preparing biogenic silver nanoparticles includes preparing an aqueous plant extract by boiling cut leaves of *Alternanthera bettzickiana* (Regel) G. Nicholson in distilled water, retaining the aqueous extract. The aqueous plant extracts were mixed with aqueous solutions of silver ions derived from different silver salt precursors (e.g., silver nitrate, silver sulfate, etc.). The resulting biogenic silver nanoparticles exhibit antimicrobial activity against various strains of gram-positive and gram-negative organisms, including some strains of drug-resistant microorganisms. The biogenic silver nanoparticles also exhibit anticancer activity against certain human cancer cell lines. Surprisingly, biogenic silver nanoparticles prepared from nitrate precursor exhibited greater anticancer activity than nanoparticles from sulfate precursor, while biogenic silver nanoparticles prepared from sulfate precursor exhibited greater antibacterial activity than nanoparticles from nitrate precursor.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The method of preparing biogenic silver nanoparticles includes preparing an aqueous plant extract by boiling cut leaves of *Alternanthera bettzickiana* (Regel) G. Nicholson in distilled water, retaining the aqueous extract. The aqueous plant extracts were mixed with aqueous solutions of silver ions derived from different silver salt precursors (e.g., silver nitrate, silver sulfate, etc.). The resulting biogenic silver nanoparticles exhibit antimicrobial activity against various strains of gram-positive and gram-negative organisms, including some strains of drug-resistant microorganisms. The biogenic silver nanoparticles also exhibit anticancer activity against certain human cancer cell lines. Surprisingly, biogenic silver nanoparticles prepared from nitrate precursor exhibited greater anticancer activity than nanoparticles from sulfate precursor, while biogenic silver nanoparticles prepared from sulfate precursor exhibited greater antibacterial activity than nanoparticles from nitrate precursor.

*Alternanthera bettzickiana* (Regel) G. Nicholson is a plant that belongs to the Amaranthaceae family. It is used as an edible vegetable in southeast Asia and India. In the present method, the leaves of *A. bettzickiana* are used to prepare an aqueous extract, which is then used to reduce silver ions from various precursors to produce biogenic silver nanoparticles exhibiting antibacterial and anticancer activity. The present method will be better understood upon consideration of the following examples.

Example 1

Preparation of Plant Extract

The leaves of *Alternanthera bettzickiana* (Regel) G. Nicholson were collected and washed with de-ionized water for 5 min. About 10 g of washed and finely chopped leaves were added into a 300 mL Erlenmeyer flask filled with 100 ml of sterilized double distilled water (1:10 ratio). The mixture was then boiled for 5 min and decanted. The solution was filtered with Whatman filter paper. The extracts were stored at −4° C. for further use.

Example 2

Synthesis of Biogenic Silver Nanoparticles

For the preparation of silver nanoparticles (AgNPs), one part of the leaf extract (filtrate) was treated with nine parts of $AgNO_3$ solution (0.01 M) (ratio between extract and silver nitrate was maintained at 1:9) in an Erlenmeyer flask and allowed to react at 75° C. without any disruption. In about 15 min, the color of the solution changes into brown, indicating the formation of AgNPs. The absorbance was measured using UV-Vis spectroscopy. The solution containing the synthesized AgNPs was then centrifuged at 15,000 rpm for 20 min, the suspended nanoparticles forming a pellet. The pellet was dissolved in deionized water and filtered through a Millipore filter (0.45 μm). An aliquot of this filtrate containing AgNPs was used for DLS, XRD, SEM, and TEM analysis. The same procedure was used to synthesize biogenic AgNPs from different precursor sources, such as 0.01 M $AgNO_3$ and 0.01 M $Ag_2SO_4$.

Example 3

Characterization of AgNPs by UV-Vis Spectroscopy

Figure 1:
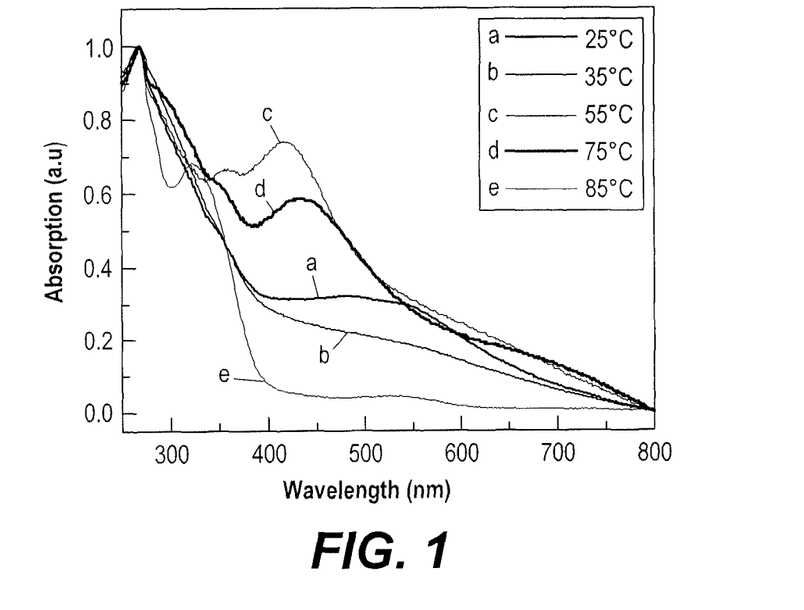
FIG. 1 is a composite of UV-Vis spectra of biogenic silver nanoparticles prepared by reducing silver ions with an aqueous extract of *A. bettzickiana* at different temperatures.

The UV-Vis spectra were recorded for biogenic synthesized AgNPs at different temperatures such as 30° C., 50° C., 75° C., and 90° C. (see FIG. 1). The brown color was formed rapidly within 15 min at 75° C. and 90° C., respectively, and no color change was observed at 30° C. and 50° C. after a period of 24 h incubation. When the samples were incubated at 75° C., $\lambda_{max}$ absorbance for biogenic synthesized AgNPs was seen at a greater visible range of 446-448 nm. The comparative UV-Vis spectra of different precursor route prepared silver nanoparticle are shown in FIG. 2D.

Example 4

Characterization of AgNPs by X-Ray Diffraction (XRD)

Figure 2A:
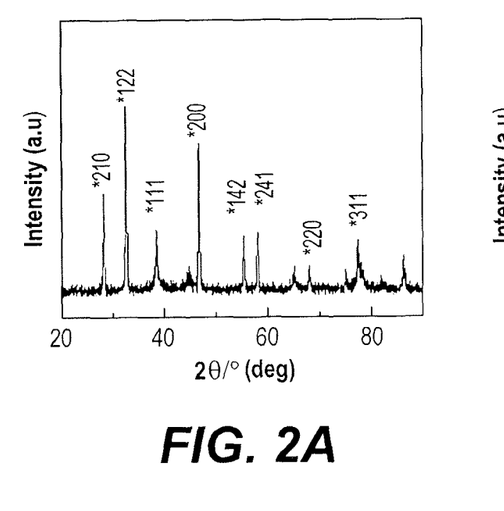
FIG. 2A is an X-ray diffraction spectrum of biogenic silver nanoparticles prepared from silver nitrate precursor.
Figure 2B:
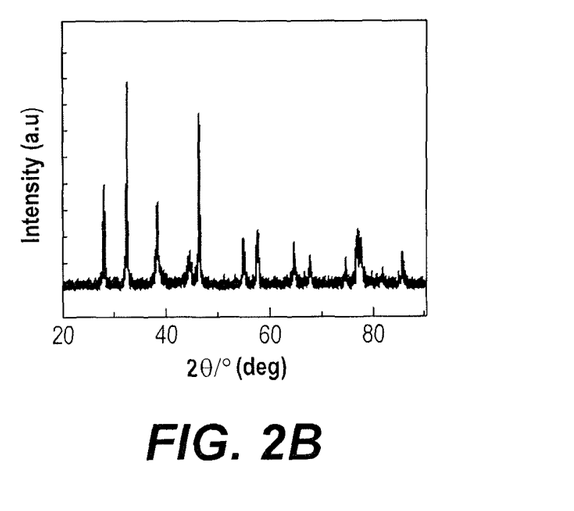
FIG. 2B is an X-ray diffraction spectrum of biogenic silver nanoparticles prepared from silver sulfate precursor.
Figure 2C:
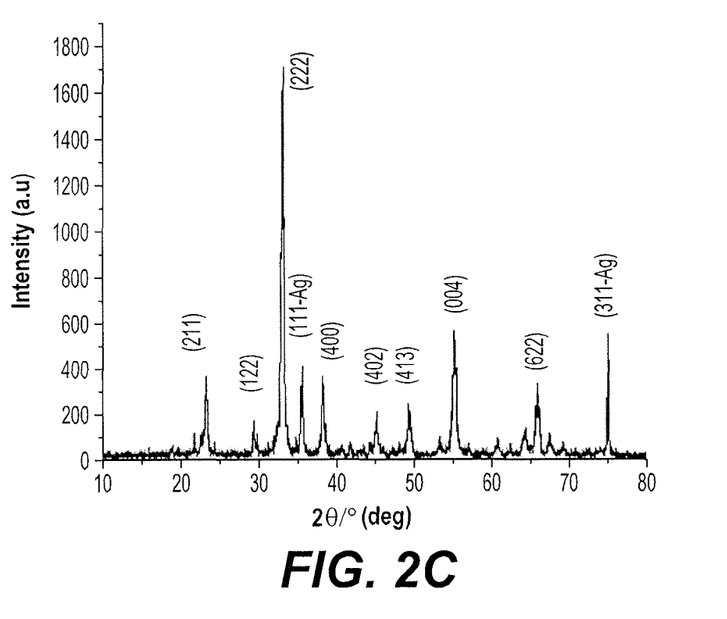
FIG. 2C is an X-ray diffraction spectrum of biogenic silver nanoparticles prepared from silver carbonate precursor.
Figure 2D:
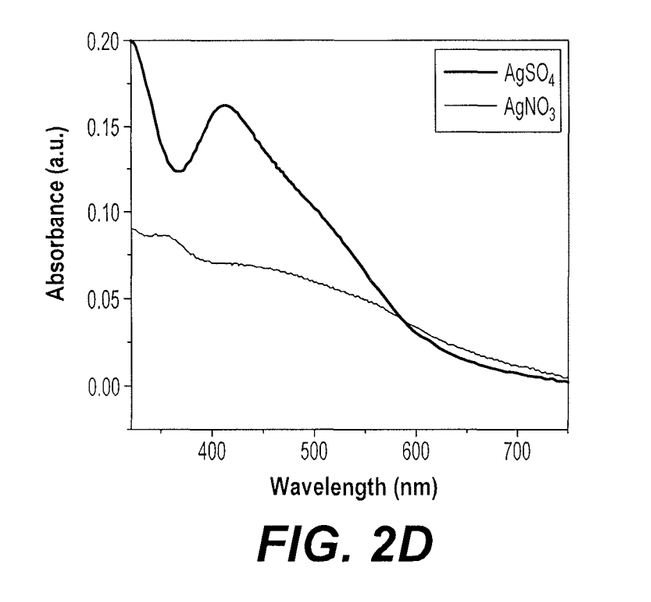
FIG. 2D is a composite comparing the UV-Vis spectra of biogenic silver nanoparticles prepared from silver nitrate precursor to those prepared from silver sulfate precursor.

The XRD pattern of the different precursor route-prepared AgNPs are shown in FIGS. 2A-2C. A number of Bragg reflection peaks were observed at 2θ values of 27.81°, 32.16°, 38.12°, 44.3°, 46.21°, 54.83°, 57.39°, 64.42° and 77.45°, which are indexed to (210), (122), (111), (200), (231), (142), (241), (220) and (311) planes, indicating the biogenic method produced AgNPs, and it forms crystals based on the face-centered cubic structure, which was matched with the JCPDS, file No. 04-0783 [30]. The XRD results confirmed that the AgNPs synthesized by the plant extract are pure and crystalline in nature. The size of AgNPs was calculated using Debye-Scherer's equation $D=0.92/(\beta \cos \theta)$, where D is the crystalline size. The crystallite sizes of AgNPs were calculated using the above mentioned formula with respect to the most intense peak (hkl value of (111) in FIGS. 2A-2B and was estimated to be around 13 nm and 15 nm, respectively, for AgNPs prepared from the nitrate and sulfate sources.

Example 5

SEM and TEM Characterization of Biogenic AgNPs

Figure 3A:
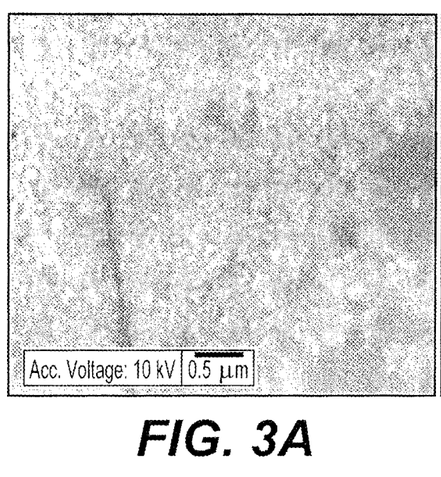
FIGS. 3A and 3B are SEM micrographs of biogenic silver nanoparticles synthesized using an aqueous extract of *A. bettzickiana* at different magnifications.
Figure 3B:
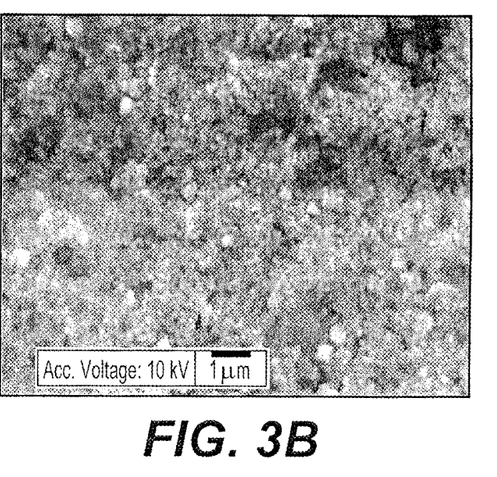
Figure 3C:
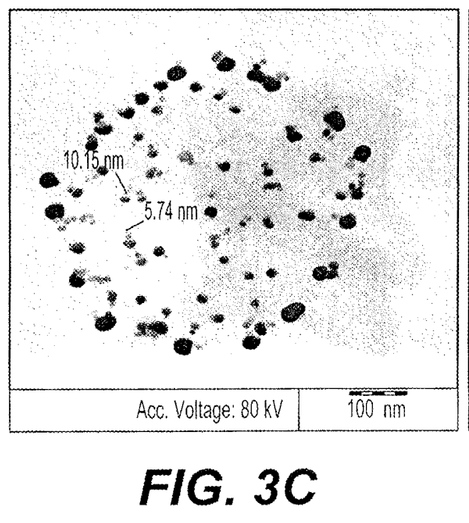
FIGS. 3C, 3D, 3E, and 3F are TEM micrographs of biogenic silver nanoparticles synthesized using an aqueous extract of *A. bettzickiana*.
Figure 3D:
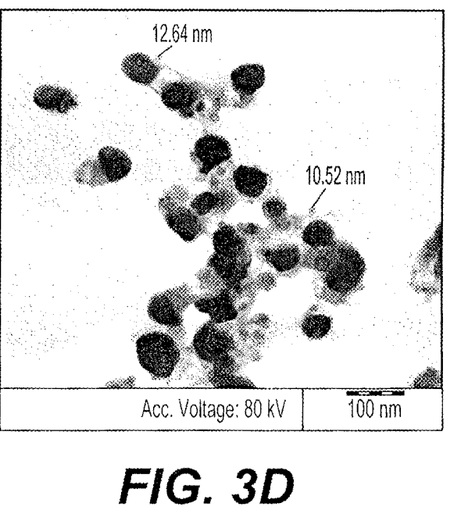
Figure 3E:
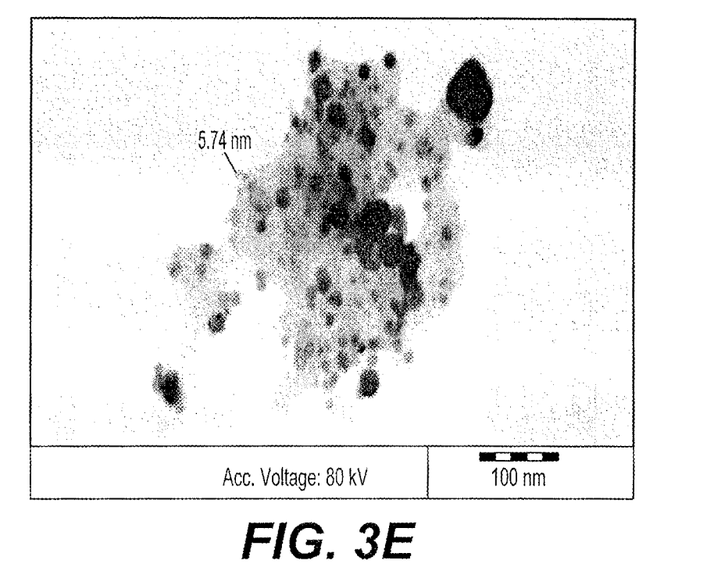
Figure 3F:
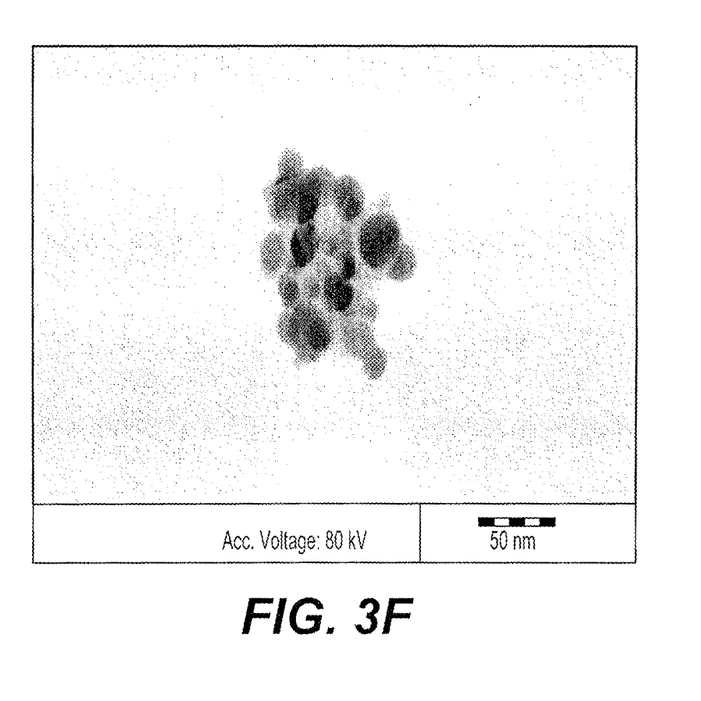

FIGS. 3A and 3B show the SEM micrographs of biogenic route prepared silver nanoparticles. SEM micrographs indicated different shapes, such as spherical, triangular and some cuboidal structures, respectively, for the biogenic synthesized AgNPs. This result revealed the formation of different sized NPs using the plant extract, including very small NPs (3-5 nm). This could be because of the quality and nature of capping agents present in the plant extract.

Figure 4A:
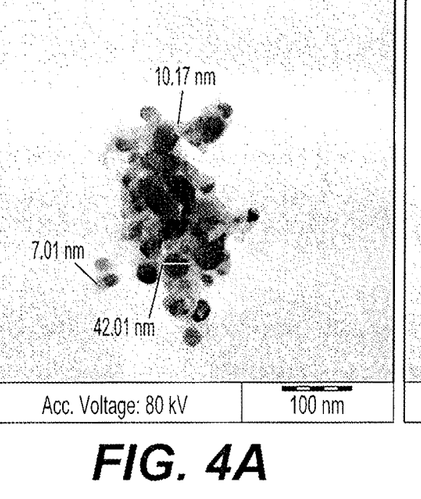
FIGS. 4A and 4B are exemplary SEM micrographs of biogenic silver nanoparticles synthesized using an aqueous extract of *A. bettzickiana* and silver sulfate precursor.
Figure 4B:
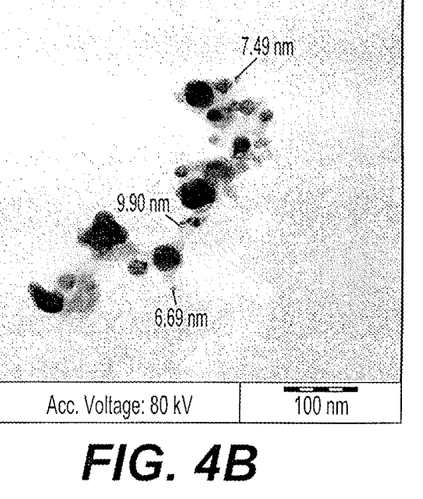
Figure 4C:
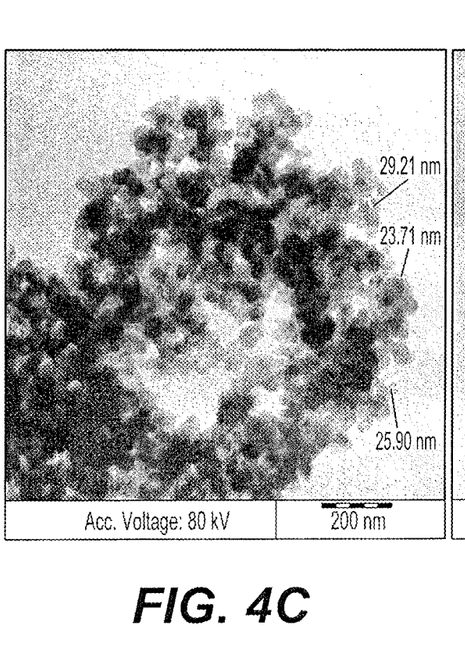
FIGS. 4C and 4D are exemplary SEM micrographs of biogenic silver nanoparticles synthesized using an aqueous extract of *A. bettzickiana* and silver carbonate precursor.
Figure 4D:
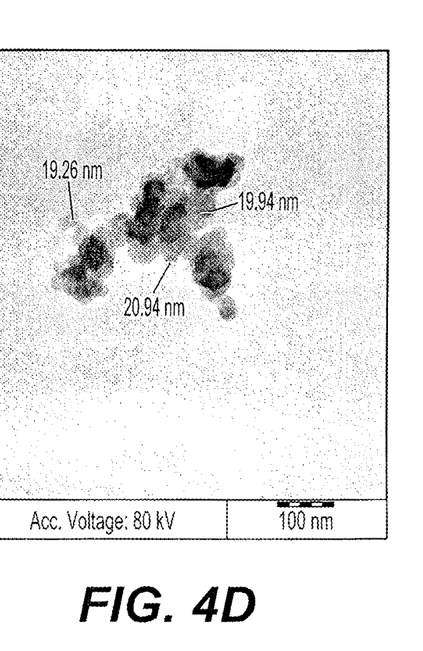
Figure 5A:
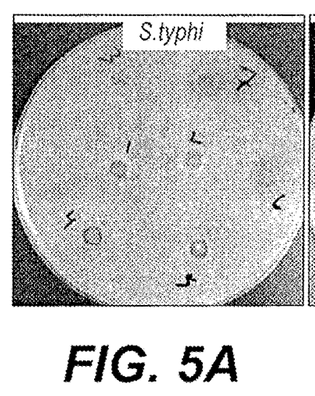
FIG. 5A is a photograph of well diffusion studies comparing the activities of silver nitrate (cell 1), pure aqueous *A. bettzickiana* extract (cell 2), and biogenic silver nanoparticles synthesized using an aqueous extract of *A. bettzickiana* and a silver precursor at various concentrations between 5-100 µg (cells 3-7) against *S. typhi*.
Figure 5B:
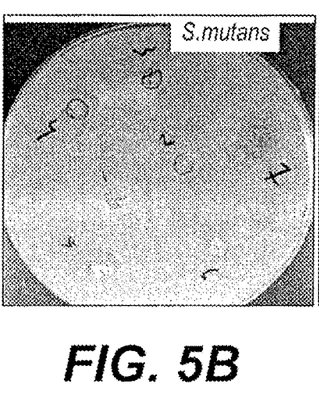
FIG. 5B is a photograph of well diffusion studies comparing the activities of silver nitrate (cell 1), pure aqueous *A. bettzickiana* extract (cell 2), and biogenic silver nanoparticles synthesized using an aqueous extract of *A. bettzickiana* and a silver precursor at various concentrations between 5-100 µg (cells 3-7) against *S. mutans*.
Figure 5C:
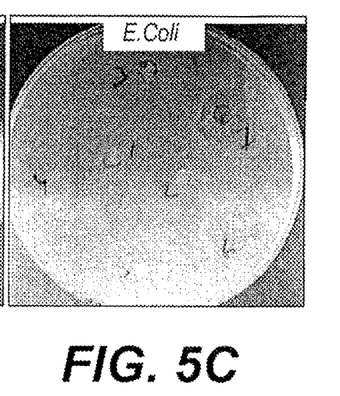
FIG. 5C is a photograph of well diffusion studies comparing the activities of silver nitrate (cell 1), pure aqueous *A. bettzickiana* extract (cell 2), and biogenic silver nanoparticles synthesized using an aqueous extract of *A. bettzickiana* and a silver precursor at various concentrations between 5-100 µg (cells 3-7) against *E. coli*.
Figure 5D:
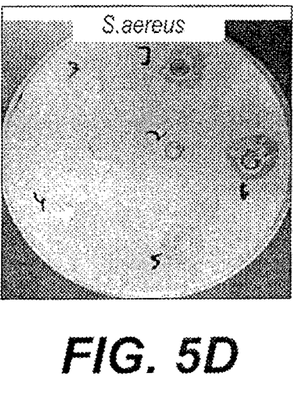
FIG. 5D is a photograph of well diffusion studies comparing the activities of silver nitrate (cell 1), pure aqueous *A. bettzickiana* extract (cell 2), and biogenic silver nanoparticles synthesized using an aqueous extract of *A. bettzickiana* and a silver precursor at various concentrations between 5-100 µg (cells 3-7) against *S. aureus*.
Figure 5E:
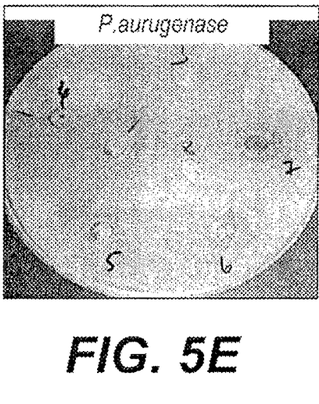
FIG. 5E is a photograph of well diffusion studies comparing the activities of silver nitrate (cell 1), pure aqueous *A. bettzickiana* extract (cell 2), and biogenic silver nanoparticles synthesized using an aqueous extract of *A. bettzickiana* and a silver precursor at various concentrations between 5-100 µg (cells 3-7) against *P. aeruginosa*.

For TEM micrographs, a powder form of AgNP (1 µg) was dispersed in distilled water. A few drops of this solution was placed on a copper-coated grid and dried at 70° C. before TEM analysis. The TEM micrographs of AgNPs prepared from silver nitrate precursor sources are shown in FIGS. 3C-3F. Very fine NPs of Ag were obtained in the AgNPs prepared using nitrate precursor, and the particle size obtained was below 5 nm and ranged up to 15 nm. Very fine metal rich NPs (black dot-type particles in FIG. 3C) are visible in the images, and no agglomeration of particles was observed. FIGS. 4A and 4B show the AgNPs prepared using the sulfate source of Ag forming little dense and metal rich NPs with size varying from 5 nm-30 nm. The conclusion obtained from comparing TEM studies confirms the presence of very small particles of Ag obtained from the nitrate source of Ag compared to the AgNPs prepared using the sulfate precursor.

TEM micrographs of biogenic synthesized AgNPs using *A. bettzickiana* plant extract confirmed the morphology and size of the NPs detected by SEM. Biogenic route synthesized AgNPs were polydispersed, and most of the particles were spherical in shape, ranging in size from 5-15 nm. Very fine nanoparticle of silver in the form of spherical dot shape as well as rectangle shapes were obtained.

Example 6

Antibacterial Activity of Biogenic AgNPs

For assessing the antibacterial activity of the AgNPs, three gram-negative bacteria (*Salmonella typhi, Escherichia coli* and *P. aeruginosa*) and two gram-positive bacteria (*Staphylococcus aureus* and *Streptococcus mutants*) were used. All cultures were obtained from King Abdul-Aziz medical hospital, Riyadh, Saudi Arabia. The cultures were stored at 4° C. for further study. For determining the antibacterial activity, bacterial young cultures (18 h) were prepared from this stock culture.

An agar well diffusion method was used to assay the effect of the synthesized biogenic NP samples and the starting materials against the above-mentioned five bacteria. Mueller-Hinton agar plates were prepared and inoculated with 1 mL (1.0×10$^7$ colony-forming units) of 18 h young bacterial cultures by spread plate method using a sterile swab. In each plate, three wells (6 mm) were made using a sterile borer. Test solution at a concentration of 1 mg/mL was prepared. Various concentrations of AgNPs, 5 µL, 10 µL, 1 µL, 25 µL, 50 µL, and 100 µL (25-100 µg/mL) were added into well number 1,2, and 3 for each bacteria. Six wells were made in a culture plate for AgNPs prepared from nitrate and sulfate sources. All the plates were incubated at 37° C. for 24 h. After incubation, the diameter of the inhibitory zones around the wells in each plate was measured by scale in millimeters. The results were tabulated and compared with crude plant extract, AgNO$_3$ solution, and biogenic synthesized AgNPs. Each test was performed three times for confirmation of results.

The assessment of antibacterial activity of biogenic AgNPs was carried out using three gram-negative bacteria (*Salmonella typhi, Escherichia coli* and *P. aeruginosa*) and two gram-positive bacteria (*Staphylococcus aureus* and *Streptococcus mutants*). Tables 1 & 2 represent the antibacterial activity of different precursor route prepared AgNPs against representative gram-positive and gram-negative bacteria using the well diffusion method.

Varying concentrations (5-100 µg/mL) of *A. bettzickiana* aqueous extract were used to analyze the antibacterial activity in vitro. The antibacterial activity assay of biogenic synthesized AgNPs using *A. bettzickiana* plant extract showed effective inhibitory action against common pathogens, such as *S. aureus, S. mutants, S. typhi, E. coli*, and *P. aeruginosa* (see FIGS. 5A-5E). The synthesized NPs exhibited higher activity at very low concentration (such as 5 µg, 10 µg, and 15 µg) against *S. aureus, S. mutants, S. typhi, E. coli*, and *P. aeruginosa* (Table 1). No antibacterial activity was observed for crude plant extract and AgNO$_3$ solution. These results confirm the specificity of the antibacterial activity of the synthesized AgNPs and support the use of this plant extract for the synthesis of NPs effective against the above-mentioned pathogenic bacteria.

AgNPs synthesized from the sulfate source exhibited significant antibacterial activity, since a 5 µM concentration of AgNPs was effective against 100 µM concentration of both gram-positive and gram-negative bacteria when compared to raw AgNO$_3$. Tables 1 and 2 show the results of the antibacterial study and confirm that a concentration of 50-100 µg/plate of AgNPs could inhibit the growth of all five bacterial cultures (*Salmonella typhi, Escherichia coli, P. aeruginosa, Staphylococcus aureus*, and *Streptococcus mutants*).

FIGS. 5A-5E show a clear zone of inhibition occurred for all bacterial pathogens from lower concentration to higher concentration. Tables 1 and 2 indicate s similar trend in antibacterial activity upon addition of 50 µg and 100 µg of AgNPs in the cultured plate. The overall order of antibacterial activity demonstrated are as follows: *Salmonella typhi* (−) >*Streptococcus mutants* (+)>*Escherichia coli* (−)>*Staphylococcus aureus*(+) *P. aeruginosa* (−). It is very clear that Ag NPs prepared from the sulfate source have shown very effective anti-bacterial activity at very low concentration.

TABLE 1

Antibacterial activity of AgNPs derived from silver nitrate

| | | | | Zone of inhibition at µg level (mm) | | | | |
|---|---|---|---|---|---|---|---|---|
| Sample | | Plant extract | AgNO$_3$ | AgNPs (µg) | | | | |
| No. | Organism | 100 µg | 1 mm | 5 | 10 | 25 | 50 | 100 |
| 1 | *S. typhi* | — | — | 112 | 13 | 15 | 17 | 17 |
| 2 | *S. mutans* | — | — | 11 | 11 | 13 | 14 | 15 |
| 3 | *E. coli* | — | — | 12 | 13 | 14 | 14 | 14 |
| 4 | *S. aureus* | — | — | — | — | — | 11 | 13 |
| 5 | *P. aeruginosa* | — | — | — | 11 | 12 | 13 | 13 |

TABLE 2

Antibacterial activity of AgNPs derived from silver sulfate

| Sample | | Zone of inhibition at µg level (mm) AgNPs concentration | | | | |
|---|---|---|---|---|---|---|
| No. | Organism | 5 (µg) | 10 (µg) | 25 (µg) | 50 (µg) | 100 (µg) |
| 1 | S. typhi | 12 | 13 | 15 | 17 | 17 |
| 2 | S. mutans | 11 | 11 | 13 | 14 | 15 |
| 3 | E. coli | 12 | 13 | 14 | 14 | 14 |
| 4 | S. aureus | — | — | — | 11 | 13 |
| 5 | P. aeruginosa | — | 11 | 12 | 13 | 13 |

Example 7

Anticancer Activity of Biogenic Silver Nanoparticles

Human HT-29 and SW620 colon cancer cell lines were obtained from the American Type Culture Collection (ATCC). The cells were grown in RPMI (Invitrogen) containing 10% heat-inactivated fetal bovine serum, 100 µg/mL streptomycin, 100 units/mL penicillin, and 2 mM L-glutamine and were maintained at 37° C. in a humidified atmosphere containing 5% $CO_2$.

Cell viability was assessed by MTT assay. Briefly, HT-29 and SW620 cells, $5 \times 10^3$ cells/well, were seeded in a 96-well plate for 24 h. AgNPs solved by sonication in ethanol (1 mg/mL) at varying concentrations (0, 2.5 µM, 5 µM, 7.5 µM, and 10 µM) was added to the cells and incubated for 24 h. After incubation, 10 µL of MTT (5 mg/ml) was added into each well for 2-4 h. The insoluble formazan crystals formed were dissolved in dimethylsulfoxide (DMSO) and quantified with a microplate reader (ELx800, BioTek, USA) at 540 nm. Survival rate percentage was measured using the formula: (Absorbance of treated sample)/(Absorbance of control)×100.

In an MTT assay, treatment of human colon cancer cell line HT-29 with different concentrations of AgNPs inhibited the increase in cell number as compared to the control (see FIGS. 6A-9B). Anticancer activity of cell viability for HT-29 & SW-620 cell lines on Ag nanoparticles prepared from nitrate precursor show a gradual increase in anti-cancer activity with respect to AgNPs concentration (see FIGS. 6A and 6B).

Figure 7A:
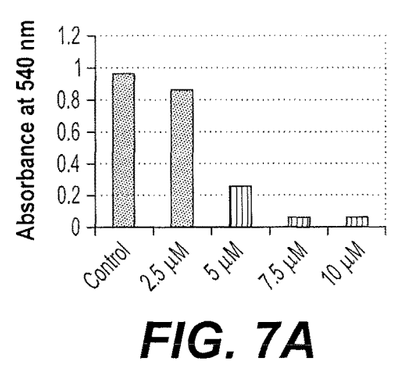
FIG. 7A is a chart showing the results of an MTT Assay of the effects of biogenic silver nanoparticles synthesized using an aqueous extract of *A. bettzickiana* and silver sulfate precursor on the HT-29 cell line.
Figure 7B:
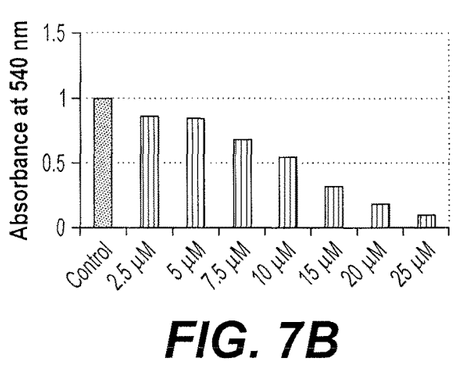
FIG. 7B is a chart showing the results of an MTT Assay of the effects of biogenic silver nanoparticles synthesized using an aqueous extract of *A. bettzickiana* and silver sulfate precursor on the SW620 cell line.

FIGS. 7A and 7B show the anticancer activity of AgNPs prepared from sulfate precursor. At higher concentration (20-30 µM) of AgNPs, addition causes the effective damage of cancer cell by silver nanoparticle. The mechanism of the anticancer activity of the biogenic synthesized silver nanoparticles may be that the accumulation of increased numbers of AgNPs inside cells results in enhanced stress, ultimately leading to cell death through generation of intracellular oxidative stress by the nanoparticles and decreasing ATP production from the mitochondria, which is a causative factor for apoptosis due to lack of cellular energy.

In our present study, the human colorectal cancer cell lines HT-29, SW620 were inhibited at very low concentrations (10 µg-15 µg). Using biogenic synthesized AgNPs may potentially prove to provide a chemotherapeutic agent in in vitro, and in future studies we plan to carry out in vivo experiments on biogenic method prepared silver nanoparticles and doped nanocomposites. In conclusion, AgNPs prepared from nitrate source is show higher anti-cancer activity compared to AgNPs prepared by sulfate precursor. The inverse activity is observed in the case of antibacterial activity for the biogenic route synthesized AgNPs. Hence, AgNPs synthesized using nitrate precursor showed enhanced and effective anticancer activity. AgNPs prepared from sulfate precursor exhibited amazing antibacterial activity against the tested bacterial pathogens (against both gram-positive and gram-negative bacteria) compared to all other samples. AgNPs synthesized by A. bettzickiana extracts confirmed that trace levels of NPs could act against colorectal cancer cell lines.

Figure 6A:
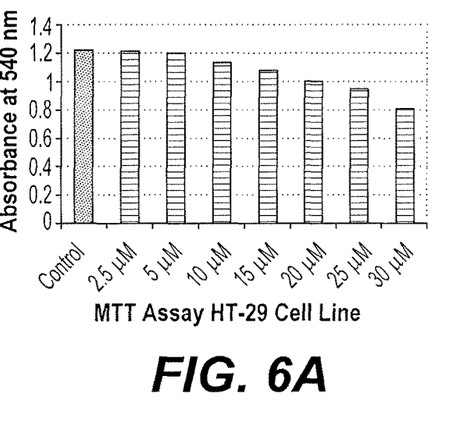
FIG. 6A is a chart showing the results of an MTT Assay of the effects of biogenic silver nanoparticles synthesized using an aqueous extract of *A. bettzickiana* and silver nitrate precursor on the HT-29 cell line.
Figure 6B:
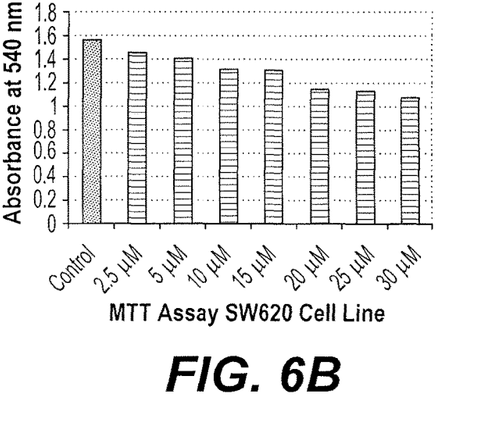
FIG. 6B is a chart showing the results of an MTT Assay of the effects of biogenic silver nanoparticles synthesized using an aqueous extract of *A. bettzickiana* and silver nitrate precursor on the SW620 cell line.
Figure 8A:
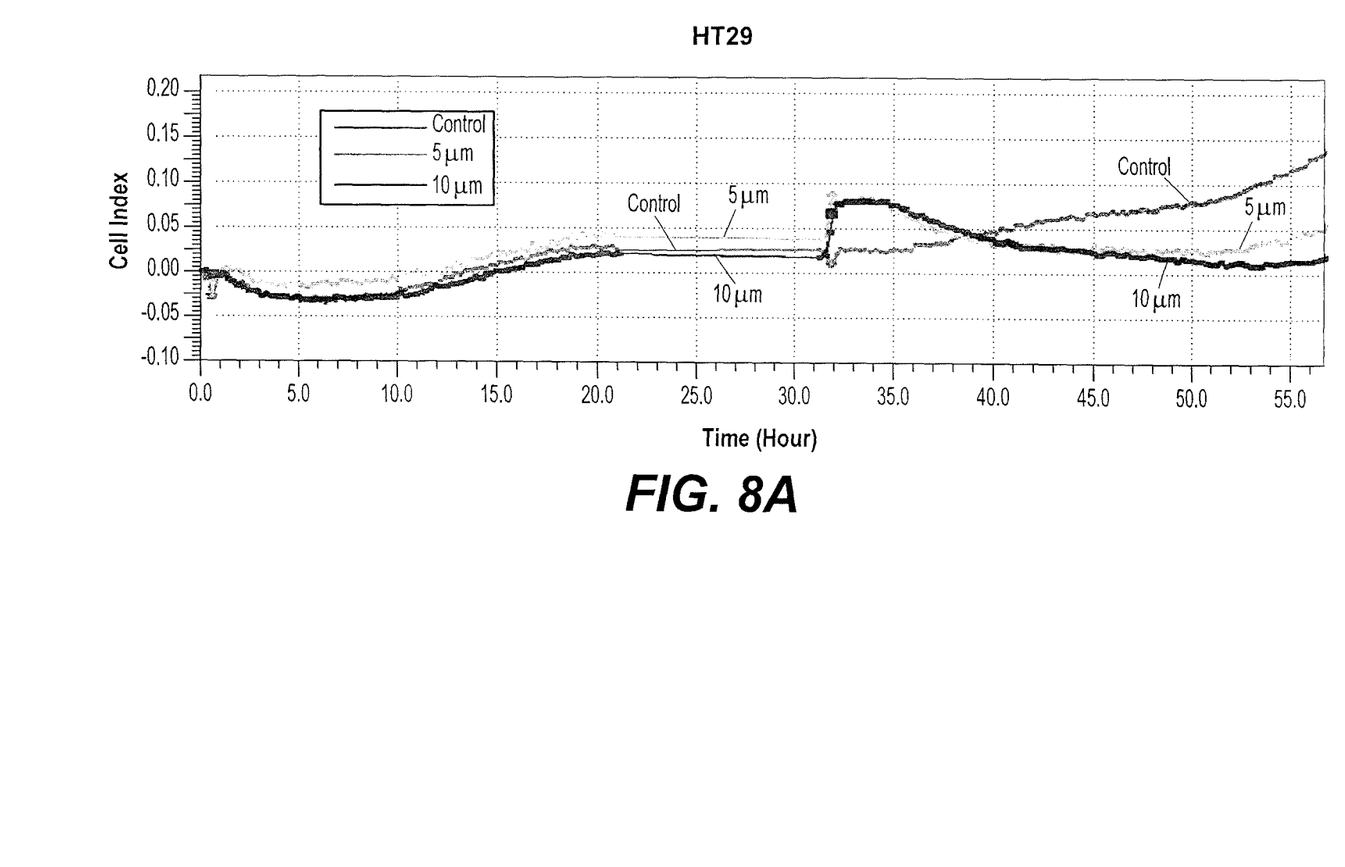
FIG. 8A is a plot of the effect of biogenic silver nanoparticles on the rate of proliferation of the HT29 cell line as provided by the xCELLigence system.
Figure 8B:
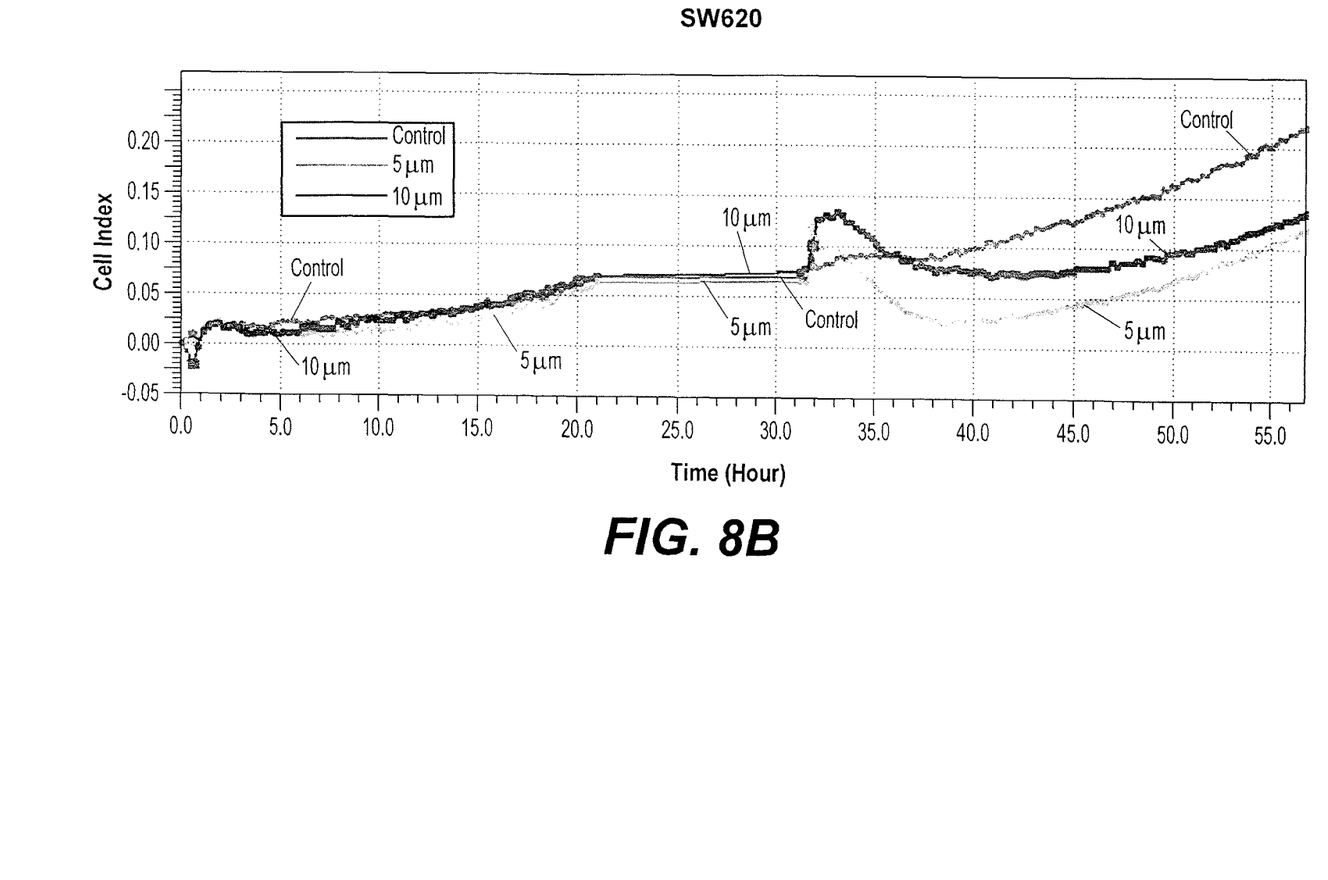
FIG. 8B is a plot of the effect of biogenic silver nanoparticles on the rate of proliferation of the SW620 cell line as provided by the xCELLigence system.
Figure 9A:
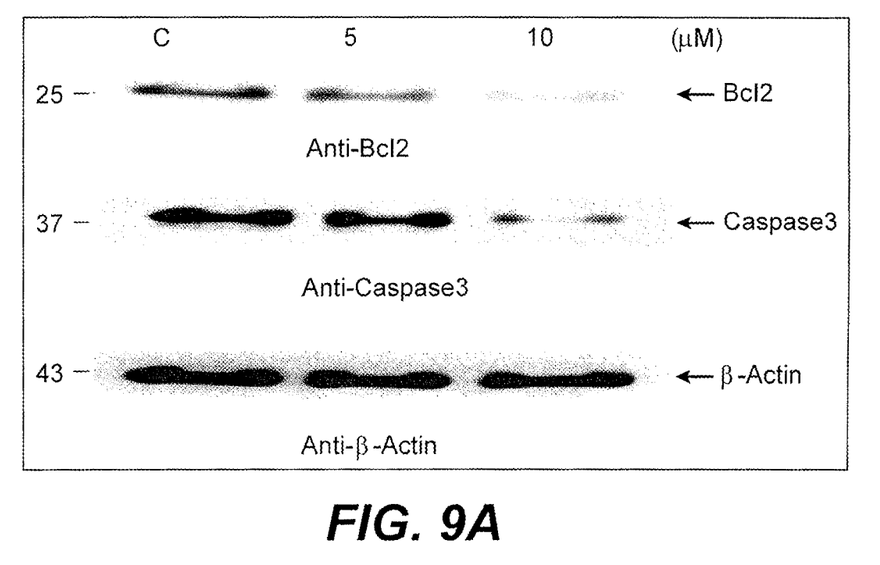
FIG. 9A is a photograph showing the results of Western blotting for the HT-29 cell line.
Figure 9B:
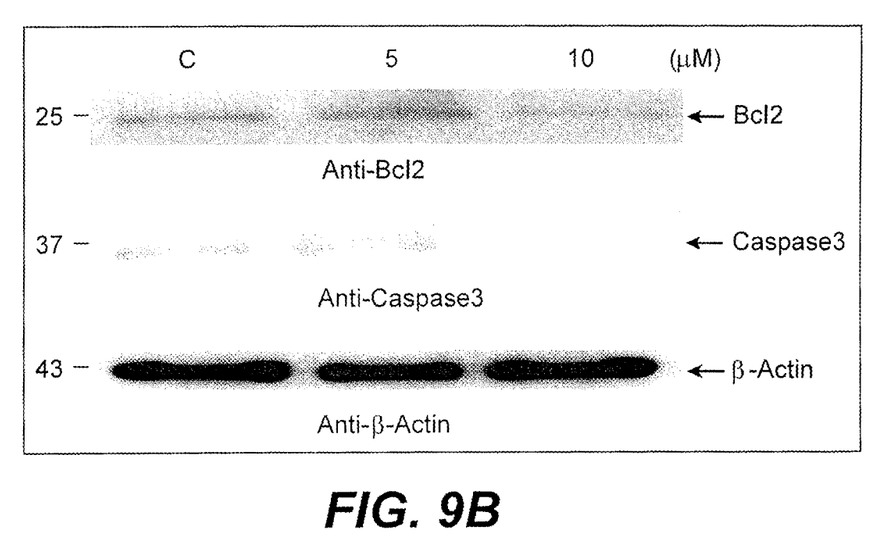
FIG. 9B is a photograph showing the results of Western blotting for the SW620 cell line.

In an MTT assay, treatment of human colon cancer cell line HT-29 with different concentration of AgNPs inhibited the increase in cell number as compared to the control (FIGS. 6A and 7A). Similar effects were observed in another colon cancer cell line, SW620 (FIGS. 6B and 7B). To further confirm the inhibition of cell proliferation by biogenic synthesized AgNPs, the xCELLigence system was used. Cells were cultured in gold-plated plates, and after 24 h, 5 µM of AgNP was added. The increase in cell number was recorded every 15 min for 30 h after AgNP addition. The results clearly indicated significant inhibition of cell proliferation by AgNP (FIGS. 8A and 8B).

Cell death or apoptosis is regulated by the interplay between pro-apoptotic (Bax, Bid, Bim) and antiapoptotic proteins (Bcl2, BclxL, Mcl1). Inhibition of antiapoptotic proteins by any drug would lead to apoptosis. Treatment of HT-29 cells with AgNPs resulted in significant decrease in the expression of Bcl2 protein (see FIG. 9A). A similar effect was observed with SW620 cells (see FIG. 9B). Bcl2 inhibition releases cytochrome from the mitochondria into cytosol and leads to the activation of an activate caspase cascade. To analyze the effects of AgNPs on caspase 3 activation, cells treated with AgNP were immunoblotted with anti-caspase3. Treatment of cells with biogenic synthesized AgNPs resulted in decreased expression of procaspase 3, suggesting the occurrence of cleavage. Thus, the synthesized AgNPs seemed to promote cell death in cultured cells.

The mechanism behind the anticancer activity of the biogenic synthesized silver nanoparticles suggests that the accumulation of an increased number of AgNPs inside cells results in enhanced stress, ultimately leading to cell death via generation of intracellular oxidative stress by the NPs and decreasing ATP production from the mitochondria, and is a causative factor for apoptosis due to lack of cellular energy.

In our present study, the human colorectal cancer cell lines HT-29 and SW620 were inhibited at very low concentrations (5 µg-10 µg) using biogenic synthesized AgNPs, which may potentially prove to be a chemotherapeutic agent in in vitro. Further studies are needed to be analyze their effect in vivo, and needed to analyze the molecular mechanism of AgNPs in the colorectal cancer cell line, normal cell line and finally on the mammalian immune system.

It is to be understood that the method of preparing biogenic silver nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of preparing biogenic silver nanoparticles, comprising the steps of:
   mixing an aqueous extract of the leaves of *Alternanthera bettzickiana* (Regel) G. Nicholson with an aqueous solution of silver nitrate to form a mixture; and heating the mixture to at least 75° C. until the mixture turns brown in color, whereby a suspension of biogenic silver nanoparticles is formed, wherein the silver nanoparticles have a particle size ranging between 3 nm-15 nm.

2. The method of preparing biogenic silver nanoparticles according to claim 1, wherein the aqueous solution of a silver salt has a concentration of 0.01 M.

3. The method of preparing biogenic silver nanoparticles according to claim 2, wherein said mixing step consists of mixing one part of an aqueous extract of the leaves of *Alternanthera bettzickiana* (Regel) G. Nicholson with nine parts of an aqueous solution of the silver nitrate.

4. The method of preparing biogenic silver nanoparticles according to claim 1, further comprising the steps of:
   collecting leaves of *Alternanthera bettzickiana* (Regel) G. Nicholson;
   washing the collected leaves in de-ionized water;
   chopping the washed leaves;
   placing the chopped leaves in distilled water as an extraction solvent to form an extraction mixture;
   boiling the extraction mixture for five minutes;
   decanting the extraction solvent from the container of boiled extraction mixture; and
   filtering the decanted extraction solvent to obtain the aqueous extract of the leaves of *Alternanthera bettzickiana* (Regel) G. Nicholson.

5. The method of preparing biogenic silver nanoparticles according to claim 4, wherein the chopped leaves and the distilled water are present in a ratio of 1:10 g/mL.

6. The method of preparing biogenic silver nanoparticles according to claim 4, further comprising the step of storing the aqueous extract at −4° C. before said mixing step.

7. The method of preparing biogenic silver nanoparticles according to claim 1, further comprising the steps of:
   centrifuging the suspension of biogenic silver nanoparticles to obtain a pellet of solid particles;
   dissolving the pellet in deionized water;
   filtering the deionized water having the pellet dissolved therein to obtain a filtrate; and
   retaining the filtrate as an aqueous suspension of biogenic silver nanoparticles.

8. Biogenic silver nanoparticles prepared according to the method of claim 1.

9. The biogenic silver nanoparticles according to claim 8, wherein the biogenic silver nanoparticles exhibit anticancer activity against the HT-29 human colon cancer cell line.

10. The biogenic silver nanoparticles according to claim 8, wherein the biogenic silver nanoparticles exhibit anticancer activity against the SW620 human colon cancer cell line.

11. The biogenic silver nanoparticles according to claim 8, wherein the biogenic silver nanoparticles exhibit antibacterial activity against both gram-positive and gram-negative bacteria.

* * * * *